United States Patent
Bengtsson et al.

(10) Patent No.: US 10,406,298 B2
(45) Date of Patent: Sep. 10, 2019

(54) NEEDLE UNIT FOR DRUG DELIVERY DEVICE

(71) Applicant: Novo Nordisk A/S, Bagsvaerd (DK)

(72) Inventors: Henrik Bengtsson, Taastrup (DK); Emil Gram Spork, Copenhagen N (DK); Lars Eilertsen, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 68 days.

(21) Appl. No.: 15/544,045

(22) PCT Filed: Feb. 19, 2016

(86) PCT No.: PCT/EP2016/053552
§ 371 (c)(1),
(2) Date: Jul. 17, 2017

(87) PCT Pub. No.: WO2016/131954
PCT Pub. Date: Aug. 25, 2016

(65) Prior Publication Data
US 2018/0264203 A1    Sep. 20, 2018

(30) Foreign Application Priority Data
Feb. 20, 2015    (EP) .................................... 15155941

(51) Int. Cl.
*A61M 5/32*    (2006.01)
*A61M 5/34*    (2006.01)
*A61M 5/50*    (2006.01)

(52) U.S. Cl.
CPC ........ *A61M 5/3293* (2013.01); *A61M 5/3272* (2013.01); *A61M 5/3286* (2013.01);
(Continued)

(58) Field of Classification Search
CPC .. A61M 5/3202; A61M 5/3213; A61M 5/347; A61M 5/3254; A61M 5/3293; A61M 5/34; A61M 5/50; A61M 2005/3217
See application file for complete search history.

(56) References Cited

U.S. PATENT DOCUMENTS

| | | | |
|---|---|---|---|
| 2008/0154192 A1* | 6/2008 | Schraga | A61M 5/329 604/110 |
| 2008/0177237 A1 | 7/2008 | Stonehouse et al. | |

(Continued)

FOREIGN PATENT DOCUMENTS

| | | |
|---|---|---|
| CN | 104093441 A | 10/2014 |
| JP | 2010519989 A | 6/2010 |
| WO | 2014064100 A1 | 5/2014 |

*Primary Examiner* — Laura A Bouchelle
(74) *Attorney, Agent, or Firm* — Wesley Nicolas

(57) ABSTRACT

The present invention provides an injection needle unit (10) comprising: a needle assembly (20) comprising: an injection needle (25) extending along a longitudinal axis and having a distal needle end configured for insertion into a subject and a proximal needle end configured for penetration of a reservoir septum, and a skirt (22) surrounding the proximal needle end and defining a receiving space (28) for reception of a needle mount of a drug delivery device, the skirt (22) comprising a slot (24), and a block structure (32) supported exteriorly of the skirt (22), wherein the block structure (32) is biased towards the longitudinal axis and is capable of radial displacement through the slot (24) from a latched position outside the receiving space (28) to a released position within the receiving space (28).

6 Claims, 3 Drawing Sheets

(52) U.S. Cl.
CPC .............. *A61M 5/347* (2013.01); *A61M 5/50* (2013.01); *A61M 5/3245* (2013.01); *A61M 2005/3254* (2013.01); *A61M 2005/3267* (2013.01); *A61M 2205/273* (2013.01)

(56) References Cited

U.S. PATENT DOCUMENTS

| | | |
|---|---|---|
| 2008/0177238 A1 | 7/2008 | Follman et al. |
| 2010/0114035 A1* | 5/2010 | Schubert .............. A61B 5/1444 604/198 |
| 2010/0234811 A1* | 9/2010 | Schubert ............... A61M 5/326 604/198 |
| 2011/0257603 A1 | 10/2011 | Ruan et al. |
| 2012/0022461 A1 | 1/2012 | Schubert et al. |
| 2013/0197477 A1 | 8/2013 | Schabbach et al. |
| 2014/0052102 A1 | 2/2014 | Nessel |
| 2014/0303555 A1 | 10/2014 | Davies et al. |
| 2014/0350479 A1 | 11/2014 | Hourmand et al. |

* cited by examiner

NEEDLE UNIT FOR DRUG DELIVERY DEVICE

CROSS-REFERENCE TO RELATED APPLICATIONS

This application is a 35 U.S.C. § 371 National Stage application of International Application PCT/EP2016/053552 (published as WO 2016/131954), filed Feb. 19, 2016, which claims priority to European Patent Application 15155941.6, filed Feb. 20, 2015; the contents of which are incorporated herein by reference.

FIELD OF THE INVENTION

The present invention relates to needle units for use with drug delivery devices to convey drug from a reservoir to an administration site.

BACKGROUND OF THE INVENTION

Administration of medication contained in sealed reservoirs often involves a penetration of the reservoir seal. For example, people with diabetes using pen injection systems for self-administration of insulin or GLP-1 attach a needle assembly comprising an injection needle to the pen injector, whereby a reservoir closure is transpierced by the injection needle, and subsequently operate the pen injector to expel a dose of medication through the injection needle and into the body.

A needle assembly for an injection device typically also comprises a skirt provided with an internal threaded section for engagement with a mating external thread on the injection device. When the needle assembly is properly attached fluid communication to the reservoir interior is established and the injection needle can be inserted through the skin of the user. To avoid the risk of contamination from growth of bacteria around the needle tip between uses it is conventionally recommended that the needle assembly be discarded after a single use. However, some people ignore this recommendation and consciously decide to use the same needle assembly again and again.

WO 2014/064100 (Novo Nordisk A/S) discloses an injection system comprising an injection device and a needle cannula, where a distal portion of the needle cannula is accommodated in a chamber when not in use, and where the chamber contains a cleaner, such that multiple use of the same needle cannula entails a reduced risk of contamination from bacteria. Even with such a solution, however, excessive use of the needle cannula may lead to other issues such as e.g. needle clogging and/or needle abrasion. Furthermore, the risk of cross-contamination arising from different users sharing the same needle cannula by using it on their respective injection devices is still present.

US 2014/0052102 (Sanofi-Aventis Deutschland GmbH) and US 2014/0303555 (Sanofi-Aventis Deutschland GmbH) both disclose a dispense interface for use with a drug delivery device which has a lockout mechanism that prevents reuse of the dispense interface after it has been used with a drug delivery device. In the former the dispense interface comprises a receiving opening configured to receive a connecting part of the drug delivery device in a spread condition of the receiving opening and to block receiving the connecting part in a relaxed condition of the receiving opening, and a spreader configured to spread the receiving opening in the spread condition. During initial attachment of the drug delivery device to the dispense interface the spreader is displaced, such that upon subsequent detachment of the drug delivery device the receiving opening automatically changes to the relaxed condition. However, the spreader is a separate element which is displaced to an inactive position during attachment of the drug delivery device, i.e. the solution requires an additional constructional part which is rendered useless upon the initial use of the dispense interface, adding to the production costs.

In the latter the process of attaching the dispense interface to the drug delivery device mechanically moves a lockout element such that once the dispense interface is detached the lockout element mechanically blocks a reattachment of the dispense interface to any drug delivery device of the same kind.

None of these prior art lockout solutions appear to be useable for conventional injection systems within diabetes care, where e.g. a pen type injection device is provided with a threaded interface and configured to receive an injection needle assembly with a mating thread, as they are both designed for use in a system where the drug delivery device and the dispense interface are attached, respectively detached, by simple axial relative motion.

SUMMARY OF THE INVENTION

It is an object of the invention to eliminate or reduce at least one drawback of the prior art, or to provide a useful alternative to prior art solutions.

In particular, it is an object of the invention to provide a needle unit having a configuration which enables it to be prevented from being used on more than one injection device, or used more than once.

It is a further object of the invention to provide such a needle unit having a small number of constructional parts.

It is an even further object of the invention to provide such a needle unit which is relatively inexpensive to produce.

In the disclosure of the present invention, aspects and embodiments will be described which will address one or more of the above objects and/or which will address objects apparent from the following text.

In an injection needle unit embodying the principles of the invention a block structure is capable of relative radial displacement with respect to a skirt having an opening between a first relative position in which the block structure is outside an interior space enclosed by the skirt and a second relative position in which the block structure extends through the opening and into the interior space. Thereby, the block structure may act to prevent full entry of a connector portion of a drug delivery device into the interior space and thereby attachment of the injection needle unit to the drug delivery device. In that connection it is noted that the block structure may be rigid (i.e. form-stable under normal use conditions) or flexible to a degree which may allow partial entry of the connector portion of the drug delivery device to a certain point within the interior space, insufficient to provide for engagement with the skirt.

In one aspect the invention provides an injection needle unit as defined in claim 1. It is clear that the longitudinal axis referred to in the claim is the central axis of the injection needle.

Thus, an injection needle unit may be provided comprising a) a needle assembly for attachment to a drug delivery device, where the needle assembly comprises an injection needle and a skirt (e.g. at least partially cylindrical) having a slot, opening, cut-out, or other type of free passage, and b) a rigid block structure being irreversibly movable from a first radial position in which the needle assembly is attached to a drug delivery device, or in which attachment of the needle assembly to a drug delivery device is enabled, to a second radial position in which attachment of the needle assembly to a drug delivery device is prevented.

The injection needle may be held in a conventional manner in a needle hub, as e.g. known from the so-called pen needles, such that a front needle comprising a distal needle end for penetration of a human skin barrier protrudes in a distal direction from the needle hub and a back needle comprising a proximal needle end for penetration of a reservoir septum protrudes in a proximal direction from the needle hub. The skirt may extend in the proximal direction from the needle hub so as to surround the back needle and define a receiving space for reception of a connector portion of a drug delivery device, such as an injection device, e.g. of the pen injector type. The block structure may be biased towards the second radial position, e.g. by a spring structure such as a compression spring or a leaf spring, and maintained in the first radial position until release of a latch means.

Such a construction allows unhindered initial attachment of the drug delivery device to the injection needle unit while it enables permanent prevention of re-attachment of the drug delivery device, or any other like device, following detachment from the injection needle unit. It may thus be ensured that the injection needle is used with one drug delivery device only, and that it in practice is rendered useless following an emptying of that drug delivery device.

Since the block structure is initially latched outside the receiving space there are no obstacles for initial entry of the needle mount into that receiving space, and the skirt may therefore comprise an interior thread for engagement with a threaded portion of the needle mount, allowing for a coupling of the injection needle unit and the drug delivery device as conventionally used in the art of injection pen systems. Alternatively, or additionally, the skirt may comprise a radially inwardly protruding stud for engagement with a bayonet track on the needle mount, or an interior bayonet track for reception of a radially outwardly protruding stud on the needle mount.

The interior thread may be arranged distally of the slot, whereby when the block structure takes up the released position it protrudes into the receiving space proximally of the interior thread, i.e. closer to the entrance to the receiving space, preventing a needle mount from reaching far enough into the receiving space to engage with the interior thread. An attachment of the drug delivery device to the injection needle unit is thus rendered impossible.

In particular embodiments of the invention the injection needle unit further comprises an outer cover at least partially surrounding the skirt. The outer cover supports the block structure and is arranged to undergo relative motion with respect to the needle assembly from a first relative position in which the block structure is in the latched position to a second relative position in which the block structure is either in the released position or in an intermediate position between the latched position and the released position. In the latched position the block structure rests on an outer, i.e. radially outwardly oriented, surface of the skirt, and a relative motion between the outer cover and the needle assembly from the first relative position to the second relative position causes the block structure to move radially into the slot. Whether the block structure is thereby brought to the released position or only towards the released position depends on the potential presence of a needle mount in the receiving space.

The relative motion between the outer cover and the needle assembly from the first relative position to the second relative position may be rotational, translational, or any combination of rotational and translational. Furthermore, when the outer cover is said to be arranged to undergo, or to be capable of undergoing, relative motion with respect to the needle assembly from a first relative position to a second relative position, this means that the outer cover and the needle assembly are capable of relative motion from the first relative position to the second relative position, either by sole motion of the outer cover, by sole motion of the needle assembly, or by motion of both the outer cover and the needle assembly.

The block structure may protrude radially from a circumferentially extending, radially deflectable arm, either forming part of the outer cover or being rotationally fixed to the outer cover. In case of the former no additional device part is needed, as the flexible arm may conveniently be produced in e.g. the moulding process for the outer cover.

The skirt may comprise an exterior recess neighbouring the slot. The recess may extend circumferentially between the slot and a radial abutment surface which may serve to define the first relative position of the outer cover and the needle assembly. In the pre-use state of the injection needle unit, where the block structure is in the latched position, the block structure may rest in the recess and contact the abutment surface, thereby preventing relative rotational motion in one direction between the outer cover and the needle assembly. This may be beneficial in connection with a mounting of a needle assembly having an interior thread onto the drug delivery device, as the needle assembly may not itself be manipulable due to the outer cover, so a relative rotational motion in the one direction between the needle mount and the outer cover, as induced during the mounting, will provide for a progressive engagement between the interior thread and the threaded portion of the needle mount, due to the rotational fixation of the needle assembly in that one direction to the outer cover.

The relative motion between the outer cover and the needle assembly from the first relative position to the second relative position may cause a rotational, translational, or combined rotational and translational, sliding movement of the block structure along the outer surface of the skirt from the initial position next to the abutment surface to the slot. Such relative motion between the outer cover and the needle assembly may occur during dismounting of the needle assembly from the drug delivery device, where frictional forces between the interior thread and the threaded portion of the needle mount may drag the needle assembly along with the needle mount. When the block structure reaches the slot the bias provided by the radially deflectable arm urges the block structure radially inwardly into the slot. Regardless of whether the block structure protrudes through the slot or not, when positioned in the slot the block structure provides a rotational interlocking connection between the outer cover and the needle assembly, which will allow the threaded portion of the needle mount to disengage from the interior thread of the skirt during continued relative rotational motion between the needle mount and the outer cover, and thereby enable dismounting of the needle assembly from the drug delivery device.

In alternative embodiments of the invention the block structure is supported by the needle assembly itself and comprises a rigid cylinder arranged in a lateral housing on an exterior surface of the needle assembly. The cylinder is capable of a predefined, limited radial displacement under the force from a compression spring. In the latched position the cylinder is completely accommodated in the lateral housing. The axial movement of a needle mount during entry into the receiving space is adapted to move a latch and thereby release the cylinder. The presence of the needle mount prevents the cylinder from displacing into the receiving space. However, the cylinder remains under a bias force of the spring, so at detachment of the drug delivery device from the injection needle unit the spring urges the cylinder radially inwards and into the receiving space, whereby re-entry of a needle mount is rendered impossible.

In either of the above mentioned exemplary embodiments of the invention the block structure is released automatically during attachment or detachment of the needle mount onto/from the needle assembly. The release of the block structure is unavoidable due to the required relative motion between the involved components, and these exemplary solutions thus each provides a guarantee that the injection needle unit cannot be re-used after being detached from the drug delivery device.

In yet other embodiments of the invention the injection needle unit further comprises an outer cover at least partially surrounding the skirt, and the block structure comprises a rigid cylinder arranged in a lateral housing fixed on an exterior surface of the outer cover. The cylinder is capable of a predefined, limited radial displacement under the force from a compression spring. In the latched position the cylinder is completely accommodated in the lateral housing. Following detachment of the injection needle unit from the drug delivery device the spring is manually releasable (e.g. by the user inducing a relative rotation between the outer cover and the needle assembly to thereby remove a support surface for the cylinder, or by the user operating a dedicated trigger button on the lateral housing to remove a latching component acting on the spring) to urge the cylinder radially through the slot and into the receiving space.

Thereby, the user may manually indicate to himself that the particular needle assembly has been used. Such indication may be relevant in case the injection needle unit further comprises e.g. a movable needle shield adapted to cover the distal needle end before and after use, because if the distal needle end is not visible and the used needle unit is for some reason not discarded immediately after use, it may be difficult to verify if the injection needle has in fact been in use, and thus there is a risk of subsequent re-application of the injection needle unit to the drug delivery device, or to another drug delivery device.

In another aspect of the invention a drug delivery system is provided comprising a drug delivery device having a needle mount with an exterior thread, and an injection needle unit as described in the above having an interior thread for engagement with the exterior thread. The injection needle unit may be pre-mounted on the drug delivery device, whereby the exterior thread is releasably connected with the interior thread when supplied to the user. The drug delivery system is thus ready to use without the user having to connect the drug delivery device and the injection needle unit first.

It is noted that although the present invention in the foregoing has been described in relation to the treatment of diabetes this is just an exemplary use. The disclosed injection needle unit is not limited to the diabetes care segment as it is indeed useable in any medical treatment system where a drug delivery device and a dispense element, such as an injection needle or an infusion set, are coupled to enable drug delivery to a desired administration site. For the same reason the needle assembly need not be of the type normally used for subcutaneous injection in the treatment of diabetes. For example, instead of a needle tube a catheter may be employed together with an IV cannula or an epidermal patch.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

When in the following relative expressions, such as "clockwise" and "counter-clockwise", are used, these refer to the appended figures and not necessarily to an actual situation of use. The shown figures are schematic representations for which reason the configuration of the different structures as well as their relative dimensions are intended to serve illustrative purposes only. Specifically, any rotational motion is described as observed when looking in the distal direction, i.e. as seen from the left side of the figure.

Figure 1:
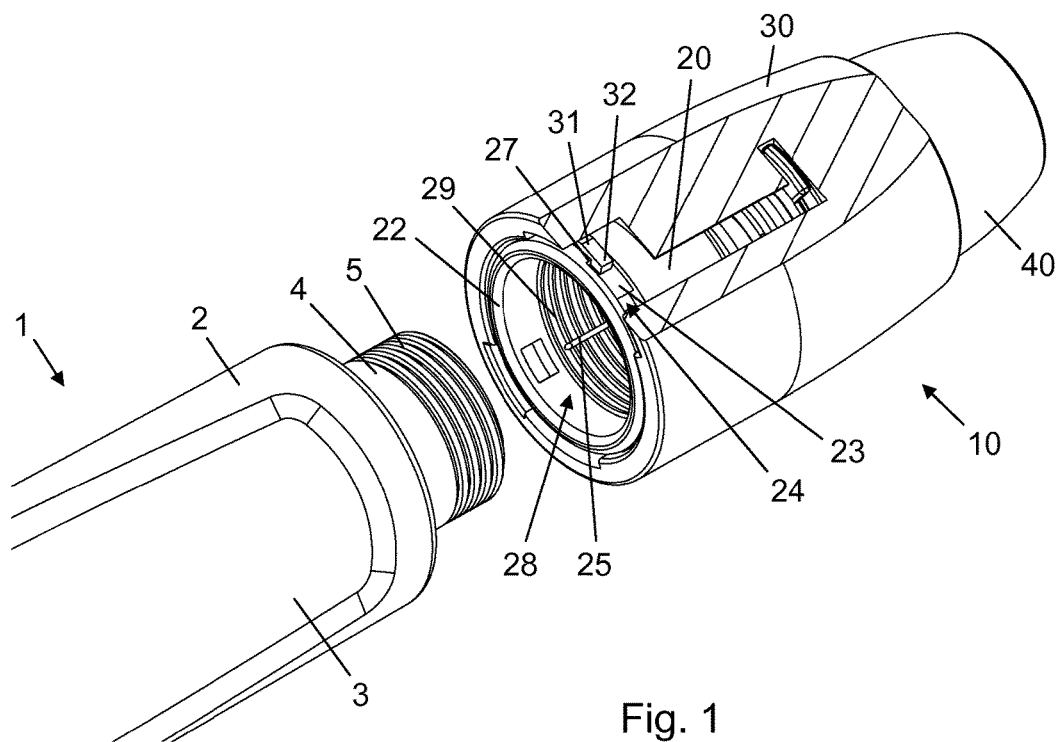
FIG. 1 is a perspective view of an injection needle unit according to an embodiment of the invention, where a portion of the injection needle unit has been cut away, and an injection pen, in a disconnected state.

FIG. 1 is a perspective view of a needle unit 10 according to a preferred embodiment of the invention. The needle unit 10 is shown just distally of a distal end portion of an injection pen 1 which is ready for attachment to the needle unit 10.

The needle unit 10 comprises a needle assembly 20, an outer cover 30 surrounding the needle assembly 20, and a needle shield 40. The needle assembly 20 comprises a needle hub 21 (see FIG. 3) in which an injection needle 25 is fastened, e.g. by use of glue, such that a portion, known as the front needle, extends axially in a distal direction therefrom and another portion, known as the back needle extends axially in a proximal direction therefrom. The injection needle 25 has a distal needle tip (not visible), which is adapted to be inserted through a skin portion of a subject user, and a proximal needle tip (visible in FIG. 1), which is adapted to penetrate a pierceable wall of a drug reservoir.

A cylindrical skirt 22 extends in a proximal direction from the needle hub 21 along the back needle and encircles the proximal needle tip. For the sake of clarity a portion of the outer cover 30 has been removed to allow inspection of an exterior portion of the skirt 22. The outer surface of the skirt 22 is provided with structural irregularities in the form of a pair of circumferentially extending diametrically opposite recesses 23 (only one is visible) and a corresponding pair of openings 24. In the following the blocking mechanism associated with these structural irregularities is described only in respect of one of the pair of recesses 23 and openings 24, it being understood that a similar action is taking place at the other of the pair of recesses 23 and openings 24.

The recess 23 extends between the opening 24 and an edge 27, which edge 27 is configured for abutment with a radial protrusion 32 arranged at the end of a bendable arm 31. The bendable arm 31 is supported by an interior surface of the outer cover 30 and is configured for radial deflection. It is noted that in the present embodiment the bendable arms 31 are unitary portions of the outer cover 30, however, one or both of them could alternatively be a separate element being fastened to the outer cover 30. Also, the number of arms, which correspond to the number of openings, could alternatively be different from two, e.g. one, three or four.

The bendable arm 31 is formed such that the radial protrusion 32 is biased radially towards the centre axis of the outer cover. In FIG. 1 the radial protrusion 32 rests on an outer surface of the recess 23 and is as such in a tensioned state. The outer cover 30 and the needle assembly 20 are capable of relative rotation about the centre axis, but in the state of the needle unit 10 shown in FIG. 1 the needle assembly 20 is prevented from clockwise rotation relative to the outer cover 30 due to the abutment between the radial protrusion 32 and the edge 27.

The skirt 22 defines an interior space 28 adapted for reception of a needle mount 4 of the injection pen 1. The needle mount 4 is arranged at the distal end of a cartridge holder 2 which holds a cartridge 3 containing a drug substance (not visible). The cartridge 3 comprises a substantially cylindrical wall which is closed by, respectively, a pierceable rubber septum (not visible), at the distal end, and a slidable rubber piston (not shown). It is understood that the injection pen 1 further comprises means for advancing the slidable piston in the cartridge 3, e.g. in a manner known from conventional injection pens on the market.

The needle mount 4 comprises a threaded section 5 structured for engagement with an internal thread 29 in the skirt 22. The internal thread 29 is arranged distally of the openings 24, whereby the distal end portion of the needle mount 4 must pass the openings 24 in order to be able to securely connect with the needle assembly 20.

The needle shield 40 is axially moveable relative to the needle assembly 20 and the outer cover 30 between an extended position in which the distal needle tip is covered and the injection needle 25 thus is contained completely within the needle shield 40 and the skirt 22 and a retracted position in which the distal needle tip protrudes from the needle shield 40.

The needle shield 40 comprises a distal end portion which may be open or closed. In case of the latter when the needle shield 40 is in the extended position the distal needle tip is housed in a sealed chamber, which chamber may be fillable or filled with a substance containing a preservative. Thereby, in case the needle is used for multiple injections with the injection pen 1 the distal needle tip is cleaned in-between two such injections, reducing the risk of contamination.

Figure 2:
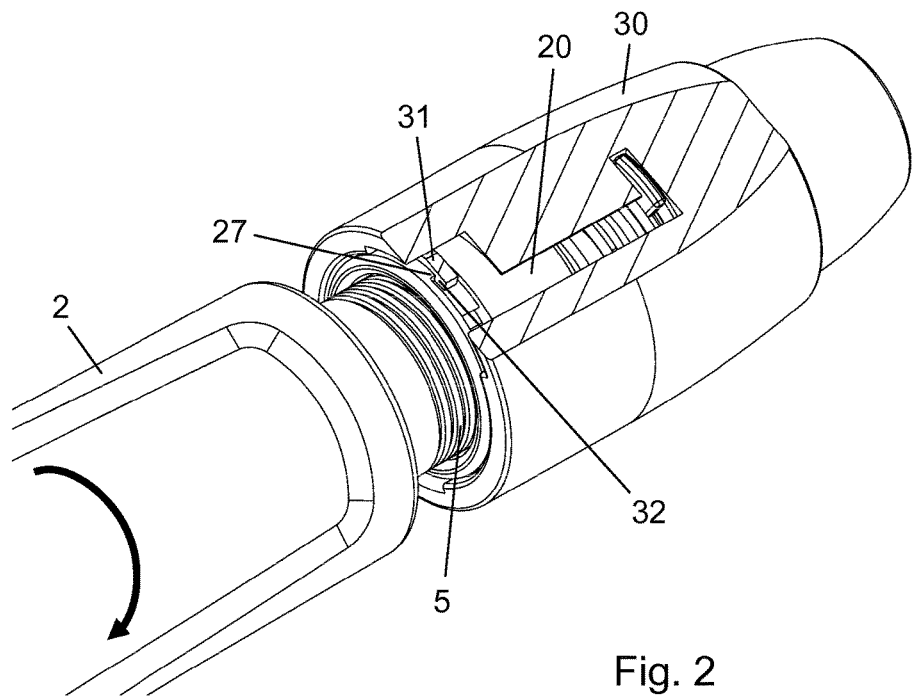
FIG. 2 shows the injection needle unit and the injection pen during connection of the two.

FIG. 2 shows the needle unit 10 and the injection pen 1 during mounting of the needle assembly 20 onto the needle mount 4. Firstly, the two are brought together by a relative axial motion and when the threaded section 5 meets the interior thread 29 the cartridge holder 2 and the needle unit 10 are made to undergo relative rotation such that the needle mount 4 undergoes a relative clockwise rotation with respect to the outer cover 30. The friction between the threaded section 5 and the internal thread 29 will tend to drag the skirt 22 clockwise as well, however, due to the abutment between the radial protrusion 32 and the edge 27 the needle assembly 20 remains stationary with respect to the outer cover 30, and a progressive engagement between the needle mount 4 and the needle assembly 20 is thereby achieved. At some point during the mounting of the needle unit 10 onto the needle mount 4 the proximal needle tip penetrates the pierceable rubber septum and establishes fluid communication with the interior of the cartridge 3.

Figure 3:
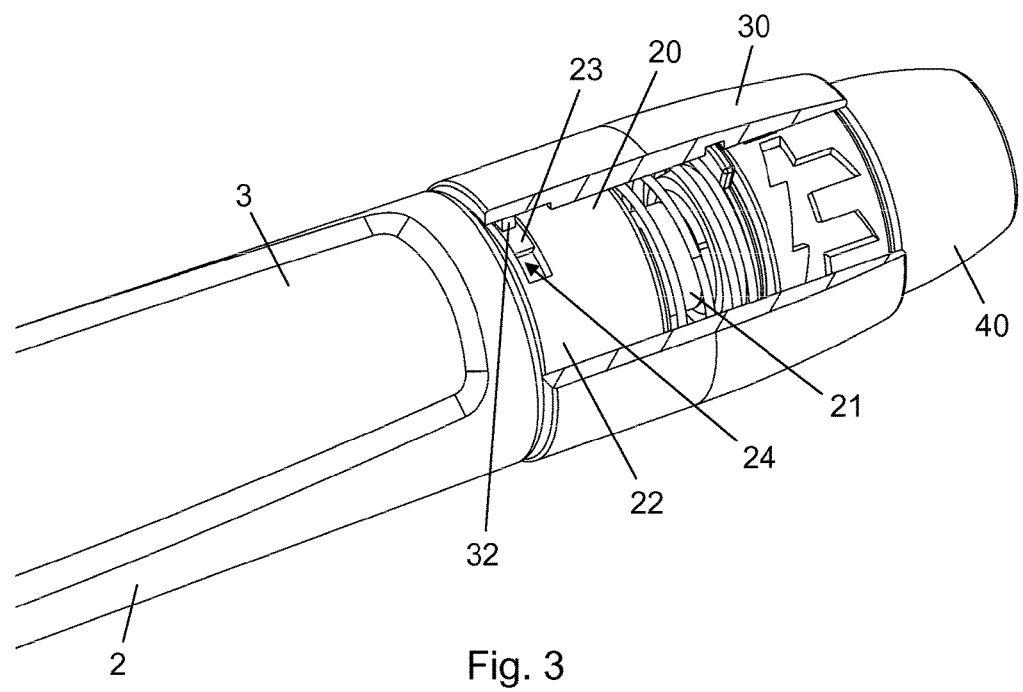
FIG. 3 shows the injection needle unit and the injection pen in a connected state.

FIG. 3 shows the needle unit 10 when fully mounted on the injection pen 1.

Figure 4:
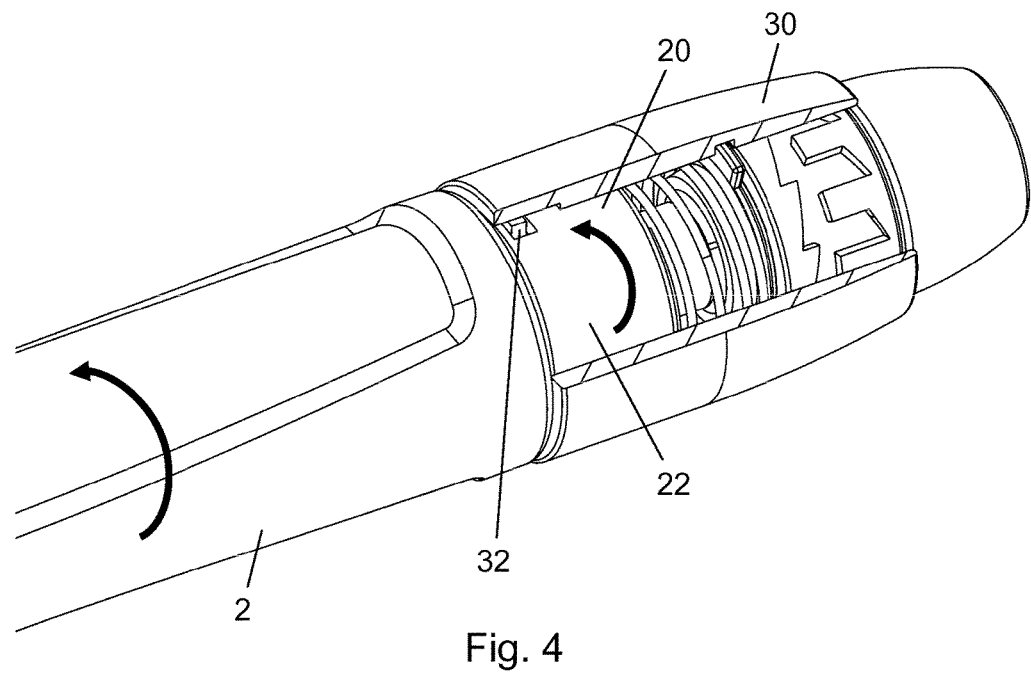
FIG. 4 shows the injection needle unit and the injection pen during disconnection.

When the needle unit 10 has been used, either for a single injection or for a plurality of injections, the needle assembly 20 is dismounted from the needle mount 4 by forcing the cartridge holder 2 to undergo a relative counter-clockwise rotation with respect to the outer cover 30. The friction between the threaded section 5 and the internal thread 29 will initially cause the skirt 22 to be dragged along with the cartridge holder 2, whereby the radial protrusion 32 slides along the outer surface of the skirt 22 in the recess 23. After a predetermined relative angular displacement between the needle assembly 20 and the outer cover 30 the radial protrusion 32 meets the opening 24 and is urged thereinto by the bias from the bendable arm 31. This is depicted in FIG. 4. At this point the bendable arm 31 is not fully released due to the presence of the needle mount 4 in the interior space 28, but the small medial deflection of the radial protrusion 32 is sufficient to rotationally interlock the needle assembly 20 and the outer cover 30.

Figure 5:
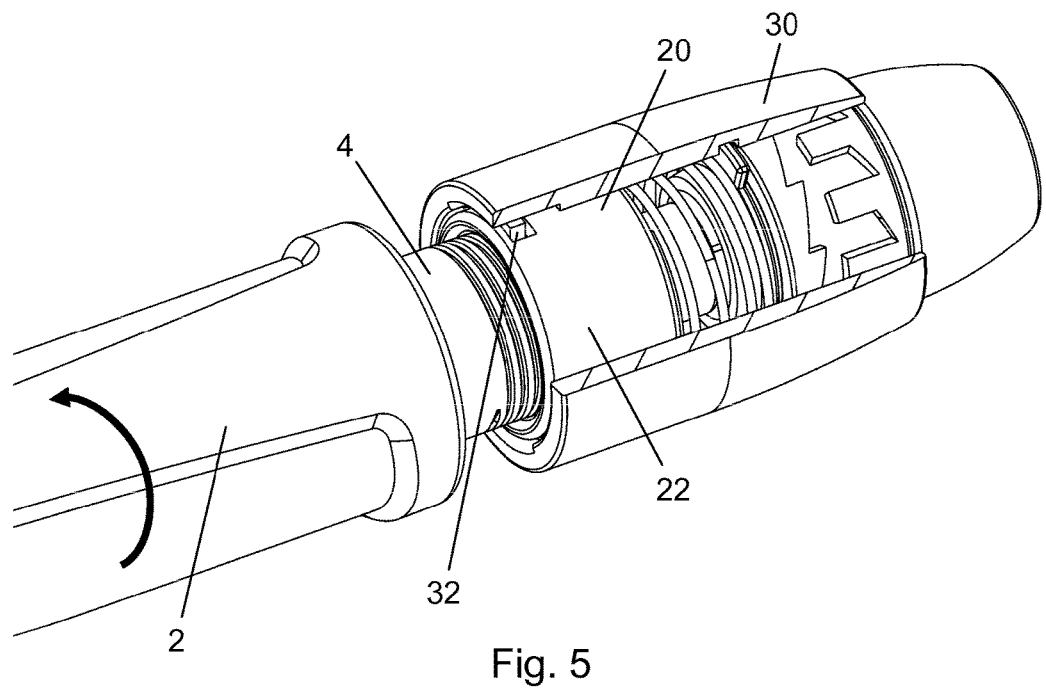
FIG. 5 shows the injection needle unit and the injection pen just before they become separated.

Further relative counter-clockwise rotation of the cartridge holder 2 with respect to the outer cover 30 thus causes a gradual unscrewing of the skirt 22 from the needle mount 4, as can be seen in FIG. 5.

When the threaded section 5 and the internal thread 29 are finally disengaged and the needle mount 4 subsequently leaves the interior space 28 by axial diverging relative motion between the cartridge holder 2 and the needle unit 10 the bias of the bendable arm 31 will cause the radial protrusion 32 to deflect further medially and thereby enter the interior space 28.

Figure 6:
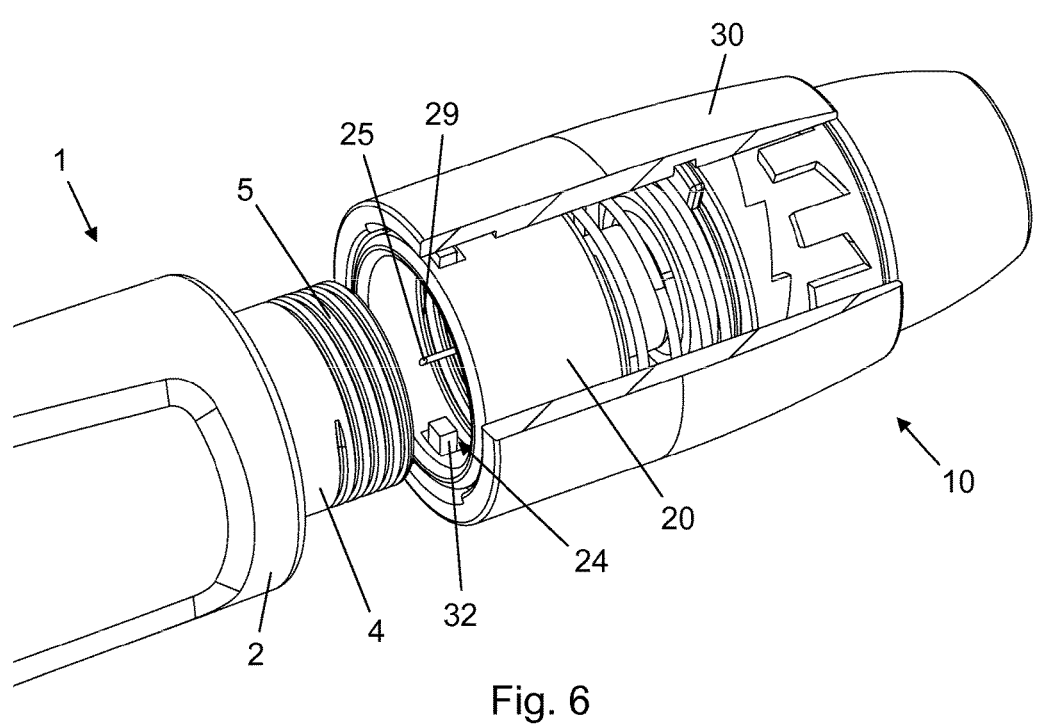
FIG. 6 shows the injection needle unit and the injection pen after disconnection.

The needle unit is now in a blocked state, as shown in FIG. 6. In this state no attachment can be made to an injection pen, as the two radial protrusions 32 will present a barrier of entry into the interior space 28 for geometries similar to that of the needle mount 4 and a mating engagement between the interior thread 29 and such geometry is thus prevented. Hence, further use of the needle unit 10 is impossible, and it is e.g. ensured that no cross-contamination can occur as a result of inadvertent or deliberate use of the used needle unit 10 with a different injection device.

In the above described preferred embodiment of the invention the needle unit 10 is available separately and is mountable onto the injection pen 1 by a user of the system. However, it is emphasized that in another preferred embodiment of the invention the needle unit 10 is pre-mounted on the injection pen 1 by the manufacturer and is thus only useable with that specific injection pen.

The invention claimed is:

1. An injection needle unit comprising:
   a needle assembly comprising:
      an injection needle extending along a longitudinal axis and having a distal needle end configured for insertion into a subject and a proximal needle end configured for penetration of a reservoir septum, and
      a skirt surrounding the proximal needle end and defining a receiving space for reception of a needle mount of a drug delivery device, the skirt comprising a slot, and
   an outer cover at least partially surrounding the skirt, the outer cover being capable of undergoing relative motion with respect to the needle assembly from a first relative position to a second relative position, and
   a block structure,
   wherein the block structure:
      is supported exteriorly of the skirt by the outer cover,
      is biased towards the longitudinal axis and is capable of radial displacement through the slot from a latched position outside the receiving space to a released position within the receiving space,
      rests on an outer surface of the skirt in the latched position, and
      is adapted to move from the latched position towards the released position in response to the outer cover and the needle assembly moving from the first relative position to the second relative position.

2. An injection needle unit according to claim 1, wherein the block structure protrudes radially from a circumferentially extending flexible arm forming part of the outer cover.

3. An injection needle unit according to claim 1, wherein the skirt further comprises an exterior recess extending circumferentially between the slot and an abutment surface,
   wherein the block structure rests in the recess in the latched position, and
   wherein in the first relative position the block structure contacts the abutment surface, preventing relative rotational motion in one direction between the outer cover and the needle assembly.

4. An injection needle unit according to claim 1, wherein in the second relative position the block structure extends into the slot, thereby rotationally interlocking the outer cover and the needle assembly.

5. An injection needle unit according to claim 1, wherein the skirt comprises an interior thread arranged distally of the slot.

6. A system comprising:
   a drug delivery device comprising a needle mount having a connecting thread, and
   an injection needle unit according to claim 5,
   wherein the connecting thread is releasably connected with the interior thread.

* * * * *